United States Patent
Sada

(10) Patent No.: US 11,096,390 B2
(45) Date of Patent: Aug. 24, 2021

(54) METHOD OF CONTROLLING WEEDS IN A CULTIVATION AREA OF FIELD CORN

(71) Applicant: SUMITOMO CHEMICAL COMPANY, LIMITED, Tokyo (JP)

(72) Inventor: Yoshinao Sada, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 159 days.

(21) Appl. No.: 16/392,253

(22) Filed: Apr. 23, 2019

(65) Prior Publication Data

US 2020/0323207 A1 Oct. 15, 2020

(30) Foreign Application Priority Data

Apr. 9, 2019 (JP) .............................. JP2019-073973

(51) Int. Cl.
| | |
|---|---|
| *A01N 43/54* | (2006.01) |
| *A01N 43/84* | (2006.01) |
| *C07D 413/04* | (2006.01) |
| *C07D 265/36* | (2006.01) |
| *C07C 233/25* | (2006.01) |

(52) U.S. Cl.
CPC ............. *A01N 43/54* (2013.01); *A01N 43/84* (2013.01); *C07C 233/25* (2013.01); *C07D 265/36* (2013.01); *C07D 413/04* (2013.01)

(58) Field of Classification Search
CPC ...... A01N 43/54; A01N 43/84; C07C 233/25; C07D 265/36; C07D 413/04
See application file for complete search history.

(56) References Cited

U.S. PATENT DOCUMENTS

| | | | |
|---|---|---|---|
| 2012/0100991 A1 | 4/2012 | Witschel et al. | |
| 2015/0119239 A1* | 4/2015 | Gewehr | A01N 61/00 504/100 |
| 2016/0194655 A1 | 7/2016 | Aponte et al. | |

FOREIGN PATENT DOCUMENTS

| | | | |
|---|---|---|---|
| CN | 105284845 A | * 2/2016 | |
| WO | WO 2010/145992 A1 | 12/2010 | |
| WO | WO-2017202774 A1 | * 11/2017 | ............. A01N 43/84 |

OTHER PUBLICATIONS

Zhang et al., CN105284845A Translation, 2016, Patent Translation powered by EPO and Google, 3 pages. (Year: 2016).*
Thomson, Julie, There's a Huge Difference Between the Corn We Eat vs. What Cow Eat, [online], HuffPost Life, 2017 [retrieved on Oct. 22, 2019], Retrieved from the Internet:<https://www.huffpost.com/entry/sweet-corn-vs-field-corn, 4 pages (Year: 2017).*
Darnton, Julia, Sweet Corn and Field Corn, What are the Differences?, 2013, MSU Extension, Michigan State University, pp. 1-2 (Year: 2013).*
Weed Control Guide, Ohio, Indiana, and Illinois, 2015, Pub#WS16/Bulletin 789/IL15, Ohio State University Extension, pp. A-216. (Year: 2015).*
Echt et al., "Evidence for the Inclusion of Controlling Elements Within the Structural Gene at the Waxy Locus in Maize", Genetics, vol. 99, Oct. 1981, pp. 275-284.
Unknown, "Sweet Corn. Field Corn. Popcorn. What's the Difference?", Best Food Facts, www.bestfoodfacts.org, Sep. 15, 2014, pp. 1-7.
Arnold et al., "Weed Control in Field Corn with Postemergence Herbicides," Research Report 709, New Mexico University, 1996, Retrieved from the Internet: <URL: https://aces.nmsu.edu/pubs/research/agronomy/RR709/welcome.html> (9 pages).
International Search Report issued in the International Application No. PCT/JP2020/015561 dated Jul. 7, 2020.
Sikkema et al., "Reduced herbicide rates provide acceptable weed control regardless of corn planting strategy in Ontario field corn," Canadian Journal of Plant Science, vol. 88, No. 2, 2008, pp. 373-378.
Written Opinion of the International Searching Authority issued in the International Application No. PCT/JP2020/015561 dated Jul. 7, 2020.

* cited by examiner

*Primary Examiner* — Sue X Liu
*Assistant Examiner* — Andriae M Holt
(74) *Attorney, Agent, or Firm* — Birch, Stewart, Kolasch & Birch, LLP

(57) ABSTRACT

The present invention can provide a method having superior crop selectivity for weed control in a cultivation area of field corn. The method includes a step of applying trifludimoxazin in a cultivation area of field corn.

3 Claims, No Drawings

METHOD OF CONTROLLING WEEDS IN A CULTIVATION AREA OF FIELD CORN

CROSS-REFERENCE TO RELATED APPLICATION

This application claims priority under 35 U.S.C. § 119(b) to Japanese Application No. 2019-073973, filed Apr. 9, 2019, the disclosure of which is incorporated herein by reference in its entirety.

TECHNICAL FIELD

The present invention relates to a method of controlling weeds in a cultivation area of field corn.

BACKGROUND ART

Hitherto, a method of treating trifludimoxazin has been known, as a method for controlling weeds in a cultivation area of corn (see Patent Document 1). Also, various types of corn such as field corn, sweet corn, popcorn, waxy corn and the like are known (see Non-Patent Documents 1, 2). However, it is not known that weeds can be controlled with particularly superior crop selectivity by applying trifludimoxazin in a cultivation area of field corn.

CITATION LIST

Patent Document

Patent Document 1: WO2010/145992

Non-Patent Document

Non-Patent Document 1: https://www.bestfoodfacts.org/corn/
Non-Patent Document 2: Genetics 99, 275-284.

SUMMARY OF THE INVENTION

Problems to be Solved by the Invention

An object of the present invention is to provide a method having superior crop selectivity for weed control in a cultivation area of field corn.

Means for Solving the Problems

The present inventor has found out that weeds can be effectively controlled with superior crop selectivity by applying trifludimoxazin in a cultivation area of field corn.

The present invention includes the following aspects [1] and [2].

[1] A method of controlling weeds in a cultivation area of field corn, the method including a step of applying trifludimoxazin in the cultivation area of field corn.

[2] The method according to [1], wherein trifludimoxazin is applied to a soil of the cultivation area of field corn.

Effect of the Invention

Weeds can be controlled in a cultivation area of field corn without causing significant injury on field corn according to the present invention.

MODE FOR CARRYING OUT THE INVENTION

The method of controlling weeds in a cultivation area of field corn of the present invention (hereinafter, sometimes referred to as "present method") includes a step of applying trifludimoxazin in a cultivation area of field corn.

Trifludimoxazin is a compound showing herbicidal activity by inhibiting protoporphyrinogen oxidase that is involved in chlorophyll biosynthesis system, and can be manufactured by a known method.

Field corn in the present method is also known as dent corn in general (see Non-Patent Document 1), and is a variety group established from *Zea mays* var. *indentata* and/or *Zea mays* var. *indurata* as major ancestors. Examples of corn which does not belong to field corn include popcorn (*Zea mays* var. *everta*), sweet corn (*Zea mays* var. *saccharata*), waxy corn (*Zea mays* var. *ceratina*), pod corn (*Zea mays* var. *tunica*), and the like.

In the present method, variations within field corn are not particularly limited as long as the field corn is a variety which is usually cultivated. For examples, field corn which belongs to diverse maturity groups from early-maturing to late-maturing can be used. Also, the variations are not limited by diverse intended usages of the harvest of field corn. For example, field corn for any of the intended usages such as seed production, ornamentals, green manures, silage, grains, and the like can be used. For grains, field corn for any of the intended usages such as starch, ethanol, oil extraction, feed, sugar production, and the like can be used. Although the weight of seeds of field corn which can be used in the present method is not particularly limited, a seed weight of field corn is usually within a rage of 100 to 400 mg/seed, more preferably 200 to 300 mg/seed.

Examples of field corn varieties include Pioneer Dent Series (for example, Pioneer 2088), Dekalb Corn Series (for example, DKC5632), MAS40F, Koshu, and the like.

The field corn may be the one producible by natural crossing, plants producible by a mutation, F1 hybrid plants, or transgenic plants (also called genetically modified plants). These plants generally have characteristics such as tolerance to herbicides, accumulation of substances harmful to insect pests, reduction in sensitivity to diseases, increase in yield potential, improvement in resistance to biotic or abiotic stress factors, accumulation of substances, and improvement in preservability and processability.

The F1 hybrid plants are those which are each a first filial hybrid obtained by crossing two different varieties with each other and usually have characteristics of heterosis, which is a nature of having more excellent trait than both of the parents. The transgenic plants are those which are obtained by introducing an exogenous gene from other organisms such as microorganisms and have characteristics like those that cannot be easily obtained by crossbreeding, mutation induction, or natural recombination in natural environments.

Examples of the technologies used to create the above plants include conventional type variety improvement technologies; genetic recombination technologies; genome breeding technologies; new breeding technologies; and genome editing technologies. The conventional type variety improvement technologies are specifically technologies for obtaining plants having desired properties by a mutation and crossing. The genetic recombination technologies are technologies in which a target gene (DNA) is extracted from a certain organism (for example, microorganism) to introduce it into a genome of a different target organism, thereby imparting new properties to the organism, and antisense technologies or RNA interference technologies for imparting new or improved characteristics by silencing a certain genes existing in plants. The genome breeding technologies are those improving breeding efficiency by using genome information and include DNA marker (also called genome markers or genetical markers) breeding technologies and genomic selection. For example, the DNA marker breeding is a method in which a progeny having a target gene with a useful trait is selected from a lot of cross progenies by using a DNA marker which is a DNA sequence and is a marker of the presence position of a gene with a specific useful trait on a genome. This method has the characteristics that the time required for breeding can be efficiently reduced by analyzing the cross progeny using a DNA marker when the progeny is a juvenile plant.

Also, the genomic selection is a technique in which a prediction formula is created from a phenotype obtained in advance and genome information to predict the characteristics from the prediction formula and the genome information without any evaluation of the phenotype and is technologies contributing to improvement in efficient breeding. The new breeding techniques are a generic term of variety improvement (=breeding) techniques that are combinations of molecular biological techniques. Examples of the new breeding techniques include cisgenesis/intragenesis, introduction of an oligonucleotide-directed mutation, RNA-dependent DNA methylation, grafting onto a GM rootstock or scion, reverse breeding, agroinfiltration, and seed production technology (SPT). The genome editing technologies are those in which genetic information is transformed in a sequence-specific manner which enables, for example, deletion of a base sequence, substitution of an amino acid sequence, and introduction of an exogenous gene. Examples of tools for these techniques include sequence-specific genome modification techniques such as zinc-finger nuclease (ZFN), TALEN, CRISPR/Cas9, CRISPER/Cpf1, and Meganuclease which each enable sequence-specific DNA scission and CAS9 Nickase and Target-AID which are each created by modifying the aforementioned tools.

Examples of the plants mentioned above include plants listed in GM APPROVAL DATABASE of genetically modified crops in the electronic information site (http://www.isaaa.org/) of INTERNATIONAL SERVICE for the ACQUISITION of AGRI-BIOTECH APPLICATIONS (ISAAA). More specifically, these examples include herbicide tolerant plants, insect pest resistant plants, disease resistant plants, and quality modified (for example, increase or decrease in content of a certain component or change in composition) plants of products (for example, starch, amino acid, and fatty acid), fertile trait modified plants, abiotic stress tolerant plants, or plants modified in traits relating to growth and yield.

Examples of plants to which tolerance to herbicides is imparted are given as follows.

The tolerance to herbicides is obtained, for example, by reducing the compatibility of a chemical with its target, by rapid metabolism (for example, breakdown or modification) resulting from the expression of a chemical deactivation enzyme, or by inhibiting the incorporation of a chemical into a plant body or the transfer of the chemical in the plant body.

The plants to which herbicide tolerance is imparted by genetic recombination technologies include plants to which tolerances to the following inhibitors are imparted by genetic recombination technologies: 4-hydroxyphenyl pyruvate dioxygenase (hereinafter abbreviated as HPPD) inhibitors such as isoxaflutole and mesotrione, acetolactate synthetase (hereinafter abbreviated as ALS) inhibitors such as imidazolinone type herbicides including imazethapyr and sulfonylurea type herbicides including thifensulfuron-methyl, 5-enolpyruvylshikimate-3-phosphate synthase (hereinafter abbreviated as EPSP) inhibitors such as glyphosate, glutamine synthetase inhibitors such as glufosinate, auxin type herbicides such as 2,4-D and dicamba, oxynil type herbicides including bromoxynil, and protoporphyrinogen oxidase (herein after abbreviated as PPO) such as flumioxazin.

In the present method, trifludimoxazin is usually used after making formulation by mixing with a carrier such as a solid or liquid carrier, and adding auxiliary agents for formulation such as a surfactant as necessary. In the case of making formulation, preferable formulation type is a soluble liquid, soluble granule, an aqueous suspension concentrate, oil-based liquid suspension, wettable powder, water dispersible granule, granule, aqueous emulsion, oil-based emulsion, and emulsifiable concentrate. More preferable formulation type is aqueous suspension concentrate. Moreover, a formulation containing trifludimoxazin singly as an active ingredient may be independently used or may be tank-mixed with a formulation containing other herbicide as active ingredients. Also, a formulation containing trifludimoxazin and other herbicide may be used. Also, a formulation containing trifludimoxazin and other herbicide as active ingredients may be tank-mixed with a formulation containing, as active ingredients, herbicides different from the above herbicides. The content of the active ingredients (trifludimoxazin or a total of trifludimoxazin and other herbicides) in the formulation is usually within a range of 0.01 to 90% by weight, preferably 1 to 80% by weight.

In the present invention, "a cultivation area of field corn" includes the area where field corn is growing or will grow.

In the present method, "applying trifludimoxazin in a cultivation area of field corn" includes applying trifludimoxazin to weeds growing in the cultivation area of field corn and applying trifludimoxazin to a soil of the cultivation area of field corn, and is usually conducted using a spray dilution produced by mixing a formulation containing trifludimoxazin with water. The amount of the dilution to be sprayed is usually 10 to 1000 L, preferably 100 to 500 L, and more preferably 140 to 300 L per hectare of cultivation area of field corn though no particular limitation is imposed on it.

In the present method, the application rate of trifludimoxazin is preferably 5 to 100 g, more preferably 10 to 50 g, still more preferably 25 g per hectare of the cultivation area. Examples of the specific application rates include 7 g, 8 g, 12 g, 15 g, 18 g, 20 g, 30 g, 40 g, 60 g, 80 g per hectare. These application rates can be described with "approximately." "Approximately" means plus/minus 10%, so, for example, "approximately 10 g per hectare" means "9 to 11 g per hectare."

Although a period of time for conducting the present method is not particularly limited, the period of time is usually within a range from 5 a.m. to 9 p.m., and the photon flux density at land surface of the place where the present method is conducted is usually 10 to 2500 $\mu mol/m^2/s$.

The spray pressure when conducting the present method is usually 30 to 120 PSI and preferably 40 to 80 PSI though no particular limitation is imposed on it. Here, the spray pressure is a set value just before the dilution is introduced into the nozzle.

The nozzle used in the present method may be flat-fan nozzles or drift-reducing nozzles. Examples of flat-fan nozzles include Teejet110 series and XR Teejet110 series manufactured by Teejet Company. When using these nozzles, the spray pressure is generally 30 to 120 PSI and the volume median diameter of liquid droplets discharged from the nozzle is usually less than 430 micro meter. The drift-reducing nozzle is a nozzle which leads to less drift compared with a flat-fan nozzle and which is called an air induction nozzle or pre-orifice nozzle. The volume median diameter of a liquid droplet discharged from the drift-reducing nozzle is usually 430 micro meter or more.

In the present method, seeds of field corn are seeded to the cultivation area by usual methods. The present method may be conducted before seeding and may be conducted concurrently with and/or after seeding. Namely, examples of the number of times that the present method is conducted include 1 to 3 times during the cultivation of field corn. In the case of once, the present method may be conducted once before, concurrently with, or after seeding. In the case of twice, the present method may be conducted twice except before seeding, twice except concurrently with seeding, or twice except after seeding. In the case of three times, the present method may be conducted three times before, concurrently with, and after seeding.

When the present method is conducted before seeding, the present method is conducted usually from 50 days before seeding to immediately before seeding, preferably from 30 days before seeding to immediately before seeding, more preferably from 20 days before seeding to immediately before seeding, still preferably from 10 days before seeding to immediately before seeding.

When the present method is conducted after seeding, the present method is conducted usually from immediately after seeding to before flowering, preferably from immediately after seeding to before emergence, and 1 to 6 true leaf stage of field corn.

The case where the present method is conducted concurrently with seeding is a case where a sowing machine and a spraying machine are integrated with each other.

In the present method, seeds of field corn may be treated with one or more compounds selected from the group consisting of insecticidal compounds, nematicidal compounds, fungicidal compounds, and plant growth regulators. Examples of compounds to be used for the seed treatment include neonicotinoid compounds, diamide compounds, carbamate compounds, organophosphorous compounds, biological nematicidal compounds, other insecticidal compounds and nematicidal compounds, azole compounds, strobilurin compounds, metalaxyl compounds, SDHI compounds, other fungicidal compounds, and plant growth regulators.

Target weed species controlled in the present method include the followings as examples, however they are not limited thereto.

Broadleaf weeds: Lambsquarters (*Chenopodium album*), *Kochia* (*Kochia scoparia*), Redroot pigweed (*Amaranthus retroflexus*), smooth pigweed (*Amaranthus hybridus*), Palmer amaranth (*Amaranthus palmeri*), Waterhemp (*Amaranthus tuberculatus*=*Amaranthus rudis*=*Amaranthus tamariscinus*), *Amaranthus quitensis*, Wild poinsettia (*Euphorbia heterophylla*), hairy fleabane (*Conyza bonariensis*), *Conyza sumatrensis*, marestail (*Conyza Canadensis*), common ragweed (*Ambrosia artemisiifolia*), giant ragweed (*Ambrosia trifida*).

Grass weeds (*Poaceae*): barnyardgrass (*Echinochloa crus-galli*), junglerice (*Echinochloa colona*), green foxtail (*Setaria viridis*), giant foxtail (*Setaria faberi*), large crabgrass (*Digitaria sanguinalis*), Jamaican crabgrass (*Digitaria horizontalis*), *Digitaria insularis*, Goosegrass (*Eleusine indica*), Johnsongrass (*Sorghum halepense*), Italian ryegrass (*Lolium multiflorum*), perennial ryegrass (*Lolium perenne*), rigid ryegrass (*Lolium rigidum*).

In the present method, trifludimoxazin may be used in combination with one or more other herbicides. For here, using in combination includes tank-mix, pre-mix, and sequential treatment. In the case of sequential treatment, the order of treatments is not particularly limited.

Herbicides which may be used in combination with trifludimoxazin is preferably glyphosate-potassium, glyphosate-dimethylamine, glyphosate-monoethanolamine, glyphosate-isopropylammonium, pyroxasulfone, mesotrione, isoxaflutole, metribuzine, dicamba-diglycolamine, dicamba-biproamine, dicamba-tetrabutylammonium, dicamba-tetrabutylphosphonium, glufosinate-ammonium, imazethapyr-ammonium, dimethenamid-P, pendimethalin, and saflufenacil, and more preferably, saflufenacil.

When aforementioned herbicide is used in combination with trifludimoxazin, the weight ratio of trifludimoxazin to other herbicide is usually within a range of 1:0.1 to 1:500, preferably 1:0.5 to 1:100, more preferably 1:1 to 1:10. Examples of the specific weight ratios include 1:0.2, 1:0.4, 1:0.6, 1:0.8, 1:1.5, 1:2, 1:2.5, 1:3, 1:4, 1:7, 1:15, 1:20, 1:25, 1:30, 1:40, 1:50, 1:80, 1:150, 1:200, 1:250, 1:300 and 1:400. These weight ratios may be described with approximately. Approximately means plus/minus 10%, so, for example, "approximately 1:2" means 1:1.8 to 1:2.2.

The cultivation of field corn in the present invention can be managed according to the plant-nutrition in the common crop cultivation. The fertilization system may be based on Precision Agriculture adopting variable rate application or may be conventionally uniform one. In addition, nitrogen fixation bacteria and mycorrhizal fungi may be inoculated by seed treatment.

EXAMPLES

The present invention will be explained by way of examples, but the present invention should not be limited thereto.

First, evaluation criteria for a herbicidal effect, and crop injury described in the following examples are shown.

[Herbicidal Effect and Crop Injury]

The evaluation of the herbicidal effect and crop injury is classified into 0 to 100, where the numeral "0" indicates no or little difference in the state of germination or growth of weeds or corn under test at the time of examination as comparison with untreated weeds or corn, respectively and the numeral "100" indicates the complete death of weeds or corn under test or the complete inhibition of their germination or growth of weeds or corn under test.

Example 1

A pot is filled with a soil, and then field corn, popcorn, sweet corn, waxy corn, palmer amaranth, waterhemp, *kochia*, common ragweed and marestail are sown thereto. Two days later, trifludimoxazin spray liquid (prepared by diluting trifludimoxazin formulation (an aqueous suspension concentrate containing 500 g/L of trifludimoxazin) with water) is uniformly applied onto the pot using sprayer at the amount of 200 L per hectare so that the application rate of trifludimoxazin may be 25 or 50 g per hectare. 21 days after the treatment, herbicidal effects and injuries on various corns are investigated. High herbicidal effects on all weeds are confirmed. It is also confirmed that injury on field corn is less than those on popcorn, sweet corn and waxy corn.

Example 2

A pot is filled with a soil, and then Palmer amaranth, waterhemp, *kochia*, common ragweed and marestail are sown thereto. On the same day, trifludimoxazin spray liquid (prepared by diluting trifludimoxazin formulation (an aqueous suspension concentrate containing 500 g/L of trifludimoxazin) with water) is uniformly applied onto the pot using sprayer at the amount of 200 L per hectare so that the application rate of trifludimoxazin may be 25 or 50 g per hectare. On the next day, field corn, popcorn, sweet corn, and waxy corn are sown. 21 days after sowing corns, herbicidal effects and injuries on various corns are investigated. High herbicidal effects on all weeds are confirmed. It is also confirmed that injury on field corn is less than those on popcorn, sweet corn and waxy corn.

Example 3

Three varieties of field corn, two varieties of popcorn, two varieties of sweet corn, two varieties of waxy corn, palmer amaranth, *kochia* and large crabgrass were sown to a pot filled with a soil. On the next day, a trifludimoxazin spray liquid (prepared by diluting an emuslfiable concentrate of trifludimoxazin with water) was uniformly sprayed onto the pot at the amount of 200 L per hectare so that the application rate of trifludimoxazin might be 50 g per hectare. 12 days after treatment, herbicidal effects on weeds and injury on corns were investigated. As a result, the herbicidal effect on each of the three weeds was 100. The results of evaluation of injury on corn are shown in Table A.

TABLE A

| Corn/variety | | Score at trifludimoxazin 50 g/ha |
|---|---|---|
| Field corn | Pioneer 2088 | 5 |
| | DKC5632 | 10 |
| | Koshu | 5 |
| Popcorn | Maru-pop | 50 |
| | Yuki-pop | 40 |
| Sweet corn | Rancher 82 | 30 |
| | Ohisama | 40 |
| Waxy corn | Shiro-mochi | 40 |
| | Ki-mochi | 30 |

Example 4

Four varieties of field corn, two varieties of popcorn, two varieties of sweet corn, palmer amaranth, *kochia* and large crabgrass were sown to a pot filled with a soil. On the next day, a trifludimoxazin spray liquid (prepared by diluting an emuslfiable concentrate of trifludimoxazin with water) was uniformly sprayed onto the pot at the amount of 200 L per hectare so that the application rate of trifludimoxazin might be 25 g per hectare. 13 days after treatment, herbicidal effects on weeds and injury on corns were investigated. As a result, the herbicidal effect on each of the three weeds was 100. The results of evaluation of injury on corn are shown in Table B.

TABLE B

| Corn/variety | | Score at trifludimoxazin 25 g/ha |
|---|---|---|
| Field corn | Pioneer 2088 | 0 |
| | DKC5632 | 0 |
| | Koshu | 0 |
| | MAS40F | 5 |
| Popcorn | Maru-pop | 20 |
| | Yuki-pop | 20 |
| Sweet corn | Rancher 82 | 30 |
| | Ohisama | 20 |

INDUSTRIAL APPLICABILITY

Weeds can be controlled in a cultivation area of field corn with superior crop selectivity according to the present invention.

The invention claimed is:

1. A method of selectively controlling growing weeds selected from the group consisting of *Kochia* species and *Amaranthus* species in a cultivation area of field corn, the method comprising a step of applying trifludimoxazin to growing weeds from 10 days before to immediately before seeding of field corn,
wherein the application rate of trifludimoxazin is approximately 12 g per hectare, and
wherein the field corn is not bred to be tolerant to trifludimoxazin transgenically or non-transgenically; and
wherein the field corn has no or little difference in the state of germination or growth compared with an untreated cultivation area.

2. The method according to claim 1, wherein the growing weeds are selected from the group consisting of *Kochia scoparia* and *Amaranthus palmeri*.

3. The method according to claim 1, wherein the growing weeds are *Kochia scoparia*.

* * * * *